United States Patent [19]

MacGregor

[11] 4,398,414
[45] Aug. 16, 1983

[54] ELECTRICAL FRICTION SLEEVE CONE PENETROMETER

[76] Inventor: John S. MacGregor, Townhouse 5, 76 Molesworth St., Kew, Australia

[21] Appl. No.: 285,471

[22] Filed: Jul. 21, 1981

Related U.S. Application Data

[63] Continuation-in-part of Ser. No. 92,263, Nov. 8, 1979, abandoned.

[51] Int. Cl.³ .............................................. G01N 3/00
[52] U.S. Cl. ............................................ 73/84; 73/9
[58] Field of Search ........................... 73/84, 81, 9, 12

[56] References Cited

U.S. PATENT DOCUMENTS 3,906,781  9/1975  Vlasblom ................................. 73/84
3,956,924  5/1976  Hansen et al. .......................... 73/81
3,988,923  11/1976 Elmiger et al. ......................... 73/84

FOREIGN PATENT DOCUMENTS 983514   6/1951  France .
1102731  2/1968  United Kingdom .
1215417  12/1970 United Kingdom .
1453273  10/1976 United Kingdom .
209818   3/1968  U.S.S.R. ................................. 73/84

*Primary Examiner*—Jerry W. Myracle
*Attorney, Agent, or Firm*—Bernard, Rothwell & Brown

[57] ABSTRACT

A quasi-static electrical friction sleeve cone penetrometer probe which includes a main body, portion of the body being a cone load cell connectible to a cone for measurement of cone resistance. A friction sleeve load cell is connectible to the main body, and a friction sleeve is connectible to the friction sleeve load cell for separate measurement of side friction. Each load cell has strain gauges attached around an outer surface, and balancing circuitry located within the cell. The friction sleeve is supported against lateral forces by three annular sleeves located on the main body, friction sleeve load cell and the cone.

11 Claims, 5 Drawing Figures

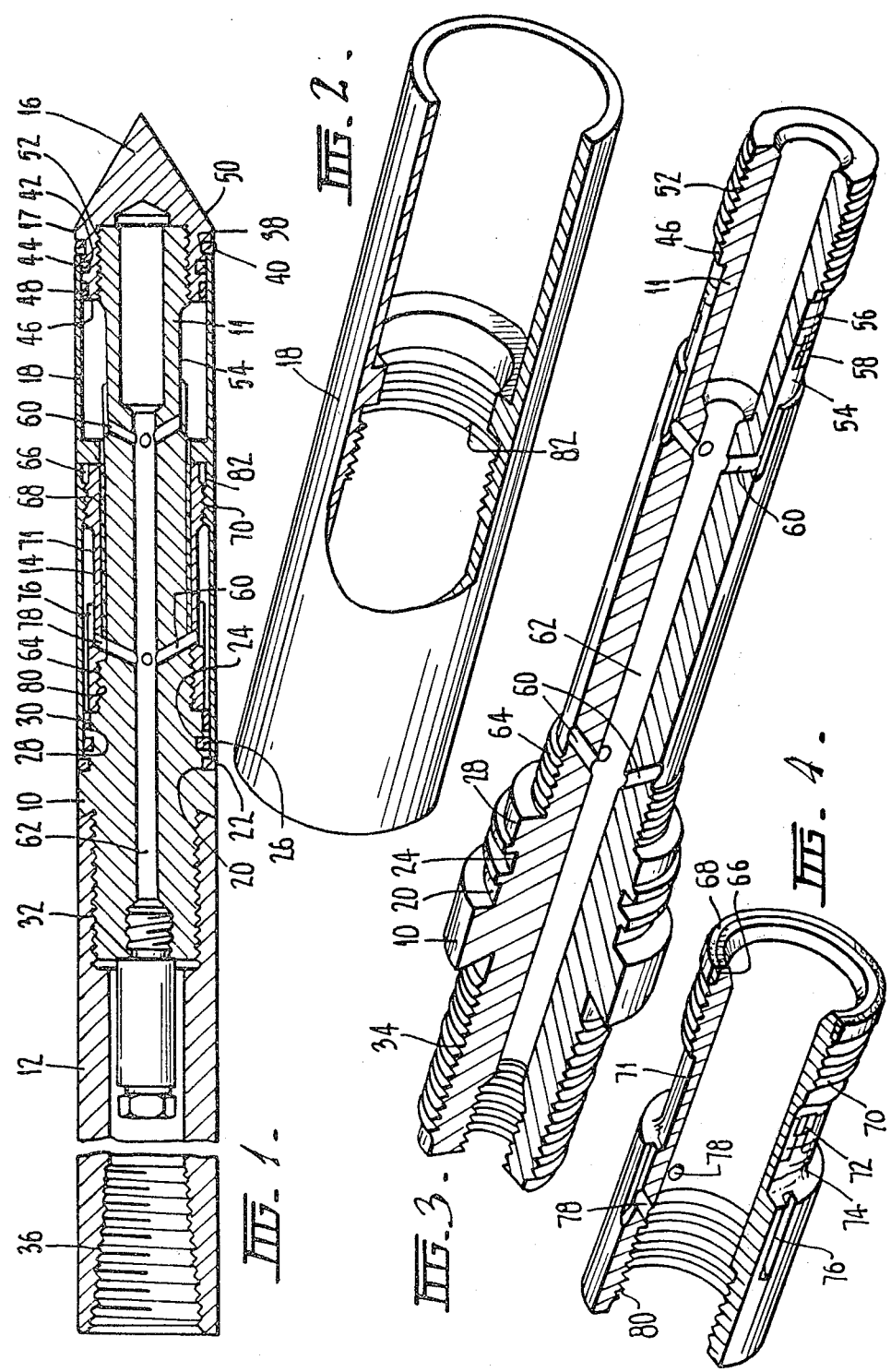

ELECTRICAL FRICTION SLEEVE CONE PENETROMETER

BACKGROUND OF THE INVENTION

1. Field of the Invention

This application is a continuation-in-part of application Ser. No. 092,263 filed Nov. 8, 1979, now abandoned.

A penetrometer is a device for measuring the penetrability of semisolids. The first penetrometer was produced by Collin in France in 1846, and for more than 100 years penetrometers were mechanical devices of increasing sophistication which included a probe portion which was pushed or driven into the ground, which produced by mechanical means an indication of the resistance of the soil to the probe.

There have developed two basic types of penetrometers, dynamic and static (actually quasi-static). This invention is concerned with quasi-static penetrometers, which are advanced into the ground at a substantially constant velocity, and produce cone resistance readings at various depths, and in particular with electric quasi-static friction sleeve cone penetrometers which have a cone for measurement of cone resistance, and a friction sleeve for measurement of side friction, and in which the measured quantities are transmitted electrically from those elements and displayed on electrically operated equipment.

Present penetrometers are most commonly used to define the natural soil profile or stratigraphy at a site. A knowledge of the geology of an area, combined with penetrometers results, enables the soil profile across the site to be determined. The description of each layer is obtained from characteristic patterns of the cone resistance (R), side friction (F), the friction ratio (F/R).

This information is an essential prerequisite to any major building construction or civil engineering project at a particular site, the only alternatives, in situ load tests on full scale foundations, laboratory test on indisturbed soil samples and in situ testing of soils, being slow and expensive.

2. Description of the Prior Art

The only practical prior quasi-static friction sleeve cone penetrometer is the Fugro, which dates from 1970, and is described in The Penetrometer and Soil Exploration by G. Sanglerat, Elsevier, 1972.

The Fugro consists of a probe which is connectable to pushing rods which are used to advance the probe into the ground from a drilling rig, usually mounted with the ancillary equipment for recording and displaying information from the probe, in a heavy motorized vehicle.

The probe consists of an adaptor for connection to the pushing rods, and a body which contains two load cell portions, one of which is connected to the cone, and the other of which is connected to the friction sleeve. Strain gauges are provided on each load cell, and wiring connected to the strain gauges is run through a cable to the recording and displaying equipment.

It should be appreciated that F is much smaller than R, in the vicinity of $10^{-3}R$, and accordingly it is essential that the smaller quantity be accurately measured. In the Fugro, F is determined by measuring F+R, and then by measuring R, and subtracting R from F+R to find F. As R and F+R are relatively large quantities, the accuracy of the value of F produced by subtraction of one of those quantities from the other is not great.

In addition, the Fugro suffers from structural weaknesses in the body and the friction sleeve, the latter being connected to the body at only one point, and being subject to lateral forces from the soil and rocks and the like encountered during advancement of the probe. The Fugro also uses mains power operated equipment in the large vehicle, which makes the setting up of a Furgo at a site complex and costly exercise.

BRIEF SUMMARY OF THE INVENTION

The invention provides, in a quasi-static electrical friction sleeve cone penetrometer, a penetrometer probe including a body, portion of which is a first load cell, and a second load cell removably attached to said body, a cone removably attachable one of said load cells, and a friction sleeve removably attachable to the other of said load cells, each of said load cells having transducers and balancing circuitry associated therewith.

It is an object of this invention to provide an improved quasi-static electrical friction sleeve cone penetrometer which produces a continuous record of cone resistance and side friction.

It is another object of this invention to provide a quasi-static friction sleeve cone penetrometer having a friction sleeve supported for resistance to lateral forces.

It is a further object of this invention to provide a quasi-static friction sleeve cone penetrometer which produces cone resistance, side friction, and friction ratio measurements of such accuracy that it may be used in the analysis of any resistive material.

BRIEF DESCRIPTION OF THE SEVERAL VIEWS OF THE DRAWINGS

FIG. 1 is a sectioned elevation of an assembled penetrometer probe, with the strain gauge and wiring details omitted;

FIG. 2 is a partly-sectioned perspective view of the friction sleeve of the probe;

FIG. 3 is a partly-sectioned perspective view of the main body and cone load cell of the probe;

FIG. 4 is a partly-sectioned perspective view of the friction sleeve load cell of the probe.

DETAILED DESCRIPTION OF THE PREFERRED EMBODIMENT

Figure 5:
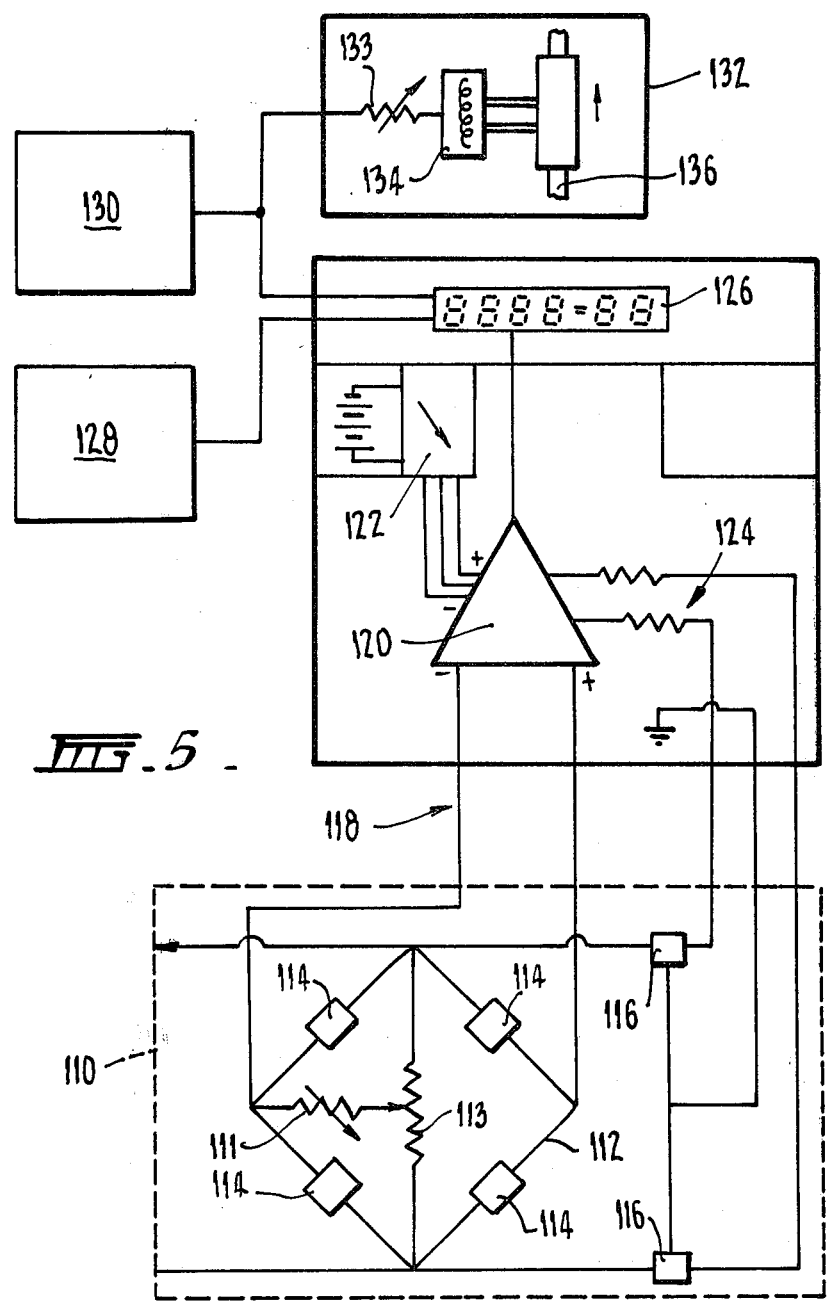
FIG. 5 is a block diagram of circuitry of the penetrometer, located within the probe and externally of the probe.

This embodiment of the invention is described in relation to the primary application of penetrometers, soil analysis and exploration. However, it must be stressed that the penetrometer of this embodiment, as a result of the accuracy of its results, may be used in the analysis of any resistive medium, such as cheese, soil conservation, detection of minerals in beach sands, forestry, ship design, archaeology, viscous fluid studies, aeronautical studies and agriculture generally.

Referring firstly to FIG. 1, there is shown a sectioned assembled penetrometer probe according to this invention. The probe consists of a main body and cone load cell 10 (shown in more detail in FIG. 3), to which is secured an adaptor 12, the elements 10 and 12 being screwed together by means of co-operating screwthreads 32. The adaptor 12 is provided with a tapering internally screwthreaded portion 36 into which the lowermost rod of a series of pushing rods (not shown, but referred to later) is screwed.

Towards the 'adaptor' end of body 10, there are provided annular grooves 20, 24, and a recessed annular shoulder 28. In these grooves there are seated respectively, O-rings 22 and 26, and an annular sleeve 30. Located next to the shoulder 28, is an externally screwthreaded portion 64 (FIG. 3) of a diameter less than that of the shoulder. The remote end of the body is a cone load cell 11, and consists of a wide annular recess 54, and an externally threaded portion 52, to which the cone 16 may be screw-fitted.

A friction sleeve load cell 14 (FIG. 4) is screwed to body 10, by the co-operation of load cell internal screwthread 80, and external body screwthread 64. The cell 14 is securely attached to body 10 by a grub screw located in an internally screw threaded aperture 78. Load cell 14 has a wide annular recess 71, and an externally screwthreaded portion 70 at the end opposite to that which is screw-fitted to body 10. An annular recessed shoulder 66 is provided at this end of the cell 14. A thin sleeve 68 of polytetrafluoroethylene is provided between portions 70 and 71 of the load cell 14 and the main body 10.

A friction sleeve 18 is secured to load cell 14 by the co-operation of the sleeve internally threaded portion 82 and load cell externally threaded portion 70. Finally, to complete the assembly of elements in the penetrometer probe, the cone 16 is screwed onto externally threaded portion 52 of body 10.

Cone 16 has annular grooves 38, 42, and a recessed annular shoulder 46, the reverse of grooves and shoulder 20, 24 and 28. Seated in the grooves, respectively, are O-rings 40 and 44, and seated on the shoulder 46 is an annular sleeve 48.

It can be seen that when friction sleeve 18 is screwed onto load cell 14, the inner end rides over sleeve 30 and O-ring 26, and abuts O-ring 22. Similarly, when cone 16 is screwed onto body 10, sleeve 48 and O-ring 44 ride under friction sleeve 18, and O-ring 40 abuts the outer end of sleeve 18.

Preferably, the O-rings are formed from a tough elastomeric material, and the sleeves 48, 68 and 30 are all formed from polytetraflouroethylene. The sleeves may be glued into place with an epoxy resin or glue. The first material provides for the absorption of shocks and limited movement, and the second material, as used in a relatively thin annular sleeve, is extremely strong, and the three sleeves thus resist lateral forces on the friction sleeve 18, which can distort sleeve friction readings. The use of thin sleeves also eliminates the need for deep grooves to seat thicker sleeves, and thus the elements of the probe are strengthened.

Apart from the O-rings and sleeves, and the strain gauges, printed circuits, balancing bridge, and cabling (to be described hereinafter) the penetrometer probe elements are preferably made from a strong, hard steel. The friction sleeve 18 is preferably of tempered steel having a hardness of between 45 and 48 Rockwell C. The cone 16 is preferably manganese tool steel, oil quenched and tempered. The strength of the cone and sleeve is an important factor, as the cone and sleeve contain the material-contracting surfaces, and weakness therein can lead to faulty results.

The cone 16 has a standard cone angle of 60°, and a conical surface area of 10 square centimeters. The cone also has a shoulder portion 17, which allows some wear of the cone surface, without allowing distortion of the friction sleeve. The friction sleeve has a cylindrical surface of 150 square centimeters. The penetrometer probe construction of FIGS. 1 to 4 enables the probe to be resistant to lateral forces on the sleeve, impacts on the cone, and bending of the main body of the probe.

The load cells 11 and 14, being connected to cone 16 and friction sleeve 18 respectively, enable simultaneous and distinct measurement of cone resistance and side friction to take place. In order to quantify these measurements, transducers in the form of strain gauges and affixed to each load cell.

On load cell 11, six double strain gauges 58 are secured to surface 54 by an expoxy glue or the like. The strain gauges, each of which has portions to measure axial and tangential stresses, are arranged symmetrically around the surface. A flexible printed circuit strip 56 is also secured to and around surface 54. The strip has staggered conductors in two rows parallel to the longitudinal axis of the strip. The gauges are electrically connected to the printed circuit, and from there the wiring is taken through an aperture 60 to the hollow central section 62 of body 10 and cell 11. In this hollow section, balancing bridge and associated circuitry (not shown in FIG. 3, but to be described hereinafter) is located, so that the temperature of the cell affects the strain gauges and the balancing circuitry. From the circuitry, the wiring extends through the hollow centre 62 into a cable (not shown) which extends through adaptor 12 and the pushing rods to the display and ancillary equipment, to be described hereinafter.

Load cell 14 has strain gauges 72 and printed circuit 74 attached to surface 71 in a similar manner; and the circuitry and wiring associated with the gauges is parallel to that of the cone load cell, the wiring from the printed circuit extending through apertures 76 to the hollow interior of the load cell.

In operation, the penetrometer probe of FIGS. 1 to 4 is pushed into the ground by a drilling rig or similar apparatus, usually hydraulically operated. The rig operates to push the pushing rods, the lowermost of which is screwed to the adaptor 12, at a carefully controlled constant rate of, preferably, 2 cm/sec. The rods are screwthreaded, internally at one end, and externally at the other, so that they may be screwed together to form a continuous rod structure which can extend to a distance of 45 m. It is desirable to use a rig which has a stable platform from which to operate. Stability and careful control of probe velocity significantly increase the accuracy of results obtained in any single test.

FIG. 5 is a block diagram of the probe strain gauge and associated circuitry and electrical equipment, which is advantageously all battery operated with rechargeable batteries. The rectangle 110 depicted in broken lines contains the electrical equipment included within one load cell. The other load cell equipment is identical, and accordingly need not be shown.

Equipment 110 includes a balancing bridge 112 which incorporates the strain gauges 114 of a load cell, a balancing potentiometer 113, and an additional potentiometer 111, which acts as a vernier adjustment to the potentiometer 113. This enables accurate balance to be undertaken within the probe, such that minimum balancing needs to be carried out at the display equipment end. Voltage regulators 116 are provided in the circuit.

The wiring from equipment 110 travels through cable 118, to amplifier 120, which is associated with a balancing net 124 and a high quality voltage regulator 122. The signal from equipment 110 is fed to a digital display 126, preferably a liquid crystal display, which provides a continuous calibrated quantitative visual readout of the cone resistance or the side friction. In practice, due to the difference in order of the quantities involved, cone resistance R is displayed in MPa, and side friction R in KPa. The signal to the display can also be fed to a microprocessor 128, for further immediate soil analysis. The signal can also be fed to a chart recorder 130, for a continuous 'hard copy' record of the measured quantities. In practice, graphs are produced of cone resistance (R), side friction (F), and friction ratio (F/R), each as a function of probe depth.

Block 132 contains circuitry which also receives the signal from the particular load cell; the circuitry operates to stop the rod pushing operation once either of the measured quantities exceeds a predetermined value, thus preventing damage to the probe.

An example is shown within block 132, where a potentiometer 133 is used to set a predetermined maximum signal level; a relay 134 is actuated when that level is reached. The relay, when actuated, acts to switch off a pushing machine, or as shown, closes a valve in the hydraulic system, part of which is designated by reference numeral 136.

The claims form part of the disclosure of this specification.

I claim:

1. A quasi-static electrical friction-sleeve cone penetrometer comprising; a generally cylindrical probe including a main body, a first load cell integral with said body and having a longitudinal axis, an independent second load cell connected to said body, said first load cell and said second load cell being axially spaced along said longitudinal axis, a cone connected to said first load cell, and a friction sleeve connected to said second load cell, said friction sleeve having an inwardly extending portion intermediate of the length thereof forming a sliding support for said sleeve on said main body between said first load cell and said second load cell, first electrical means associated with said first load cell for conversion of first load cell distortion as a result of cone resistance into electrical signals, and second electrical means associated with said second load cell for conversion of second load cell distortion as a result of side friction on said friction sleeve into electrical signals to provide a continuous and separate measurement of each quantity.

2. A penetrometer as set forth in claim 1, wherein each of said first electrical means and said second electrical means includes a series of strain gauges bonded to the external surface of the load cell, said gauges being electrically connected to a flexible printed circuit bonded to said surface, said printed circuit having two parallel rows of connectors, each row being interrupted, the interrupted portions of each row being staggered.

3. A penetrometer as set forth in claim 1, further including an amplifier for amplifying said electrical signals, a digital display for quantitatively displaying the quantities measured by said strain gauges, and chart recorders for recording cone resistance R, side friction F and friction ratio F/R.

4. A penetrometer as set forth in claim 3, further including cut-off means, operative when one of said quantities reaches a predetermined value, to prevent further advancement of the penetrometer probe.

5. A penetrometer as set forth in claim 1 wherein the probe is advanced at a controlled velocity of 2 cm/sec.

6. A quasi-static electrical friction sleeve cone penetrometer comprising a generally cylindrical probe including a main body, a first load cell integral with said body, a second load cell connected to said body, a cone connected to said first load cell, and a friction sleeve connected to said second load cell, first electrical means associated with said first load cell for conversion of first load cell distortion as a result of cone resistance into electrical signals, and second electrical means associated with said second load cell for conversion of second load cell distortion as a result of side friction on said friction sleeve into electrical signals to provide a continuous and separate measurement of each quantity; and each of said first electrical means and said second electrical means including a series of strain gauges bonded to the external surface of the corresponding load cell, each of said gauges being electrically connected to a flexible printed circuit bonded to said surface, each of said printed circuits having two parallel rows of connectors, each row being interrupted, the interrupted portions of each row being staggered.

7. A penetrometer as set forth in claim 6, wherein each of said first electrical means and said second electrical means further includes a bridge network incorporating said strain gauges and said printed circuit, the network including a balancing potentiometer and a vernier potentiometer on the movable arm of the balancing potentiometer.

8. A penetrometer as set forth in claim 6 further including an amplifier for amplifying the signals from the strain gauges, a digital display for quantitatively displaying the quantity measured by said strain gauges, and chart recorders for recording cone resistance R, side friction F and friction ratio F/R.

9. A quasi-static electrical friction sleeve cone penetrometer comprising a generally cylindrical probe including a main body, a first load cell integral with said body, a second load cell connected to said body, a cone connected to said second load cell, first electrical means associated with said first load cell for conversion of first load cell distortion as a result of cone resistance into electrical signals, and second electrical means associated with said second load cell for conversion of second load cell distortion as a result of side friction on said friction sleeve into electrical signals to provide a continuous and separate measurement of each quantity; annular sleeves provided on said main body, said second load cell or said friction sleeve, and said cone, for supporting said friction sleeve at three points against lateral forces; and each of said first electrical means and said second electrical means including a series of strain gauges bonded to the external surface of the corresponding load cell, each of said gauges being electrically connected to a flexible printed circuit bonded to said surface, each of said printed circuits having two parallel rows of connectors, each row being interrupted, the interrupted portions of each row being staggered.

10. A penetrometer as set forth in claim 9 further including an amplifier for amplifying the signals from the strain gauges, a digital display for quantitatively displaying the quantity measured by said strain gauges, and chart recorders for recording cone resistance R, side friction F and friction ratio F/R.

11. A penetrometer as set forth in claim 9, wherein each of said first electrical means and said second electrical means further includes a bridge network incorporating said strain gauges and said printed circuit, the network including a balancing potentiometer and a vernier potentiometer on the movable arm of the balancing potentiometer.

* * * * *